United States Patent [19]

Bryan

[11] Patent Number: 4,943,237
[45] Date of Patent: Jul. 24, 1990

[54] THERMOSET-THERMOPLASTIC MOLDED ARTICLE FOR DENTAL RESTORATION

[75] Inventor: Thomas T. Bryan, Mahtomedi, Minn.

[73] Assignee: Minnesota Mining and Manufacturing Company, St. Paul, Minn.

[21] Appl. No.: 303,080

[22] Filed: Jan. 26, 1989

Related U.S. Application Data

[63] Continuation of Ser. No. 932,005, Nov. 18, 1986, Pat. No. 4,850,871.

[51] Int. Cl.⁵ .............................................. A61C 11/00
[52] U.S. Cl. ..................................... 433/213; 264/16; 428/15; 428/542.8
[58] Field of Search ......................... 433/34, 60, 48, 74, 433/171, 172, 185, 196, 213, 223; 264/16, 19, 227, DIG. 64; 428/15, 542.8

[56] References Cited

U.S. PATENT DOCUMENTS

| 544,096 | 8/1895 | Griswold | 433/60 |
|---|---|---|---|
| 2,136,404 | 11/1938 | Wheeler | 22/164 |
| 2,296,877 | 9/1942 | Slack | 260/32 |
| 2,750,670 | 6/1956 | Vigg | 264/16 |
| 3,355,526 | 11/1967 | Molnar | 264/16 |
| 3,367,028 | 2/1968 | Apfel | 433/34 |
| 3,562,375 | 2/1971 | Guy et al. | 428/542.8 |
| 4,073,973 | 2/1978 | Martins et al. | 427/142 |
| 4,214,019 | 7/1980 | Donermeyer et al. | 427/142 |
| 4,215,159 | 7/1980 | Donermeyer et al. | 427/142 |
| 4,217,376 | 8/1980 | Donermeyer et al. | 427/142 |
| 4,222,976 | 9/1980 | Donermeyer et al. | 264/36 |
| 4,374,076 | 2/1983 | Stephan et al. | 264/19 |
| 4,595,364 | 6/1986 | Kusano et al. | 433/185 |
| 4,634,381 | 1/1987 | Kusano et al. | 433/172 |

OTHER PUBLICATIONS

Jansen et al., "Polymerization Shrinkage and Mircroleakage", A Paper Published in Posterior Composite Resin Restorative Materials Edited by Vanherle et al., pp. 243-262 (Peter Szulc Publishing, Co., The Netherlands, 1985).
"Powder Coatings", Krk-Othmer Encyclopedia of Chemical Technology, 3rd Ed., vol. 19, pp. 1-27 (1982).
Dental Lab Products, Article Entitled "Wax-Application System" (Jan./Feb., 1986), This Article Describes a Heated Wax Applicator for Waxup of Dental Models and Protheses.
Jordan, R. E., "Esthetic Composite Bonding" (1987).

Primary Examiner—John J. Wilson
Attorney, Agent, or Firm—Donald M. Sell; Walter N. Kirn; James D. Christoff

[57] ABSTRACT

For use in making dental restorations, a model is prepared by taking an intra-oral impression and molding in the impression a replica model made from the thermosetting resin and a thermoplastic resin. The thermosetting resin provides a tough, heat- and abrasion-resistant surface. Heat from the molten thermoplastic resin accelerates the curing of the thermosetting resin.

2 Claims, 1 Drawing Sheet

THERMOSET-THERMOPLASTIC MOLDED ARTICLE FOR DENTAL RESTORATION

This is a continuation of application Ser. No. 932,005, filed Nov. 18, 1986, now U.S. Pat. No. 4,850,871.

BACKGROUND OF THE INVENTION

1. Field of the Invention

The invention primarily concerns restorative dentistry, especially methods and devices useful for making out-of-the-mouth or extra-oral dental restorations from dental restorative or composite resin materials. The invention also concerns a model or die from which a prosthetic dental restoration can be made and a method of making such a model or die. The invention further concerns models or dies useful for such purposes as the restoration of art objects such as statues.

2. Description of Related Art

In spite of remarkable technological advances in prosthetic dental restorative or composite resin materials, amalgams typically are easier to install, can be completed in a single visit, and are regarded by many practitioners as having superior durability. For such reasons, the amalgams continue to predominate in posterior dental restorations in spite of their toxicity, aesthetically undesirable color, and the usual need to remove healthy portions of a tooth in order to interlock the amalgam into a cavity. Dental restorative or composite resins also can be applied in a single visit by being tamped into a cavity, shaped or sculptured, then cured by exposure to light and finished with a bur. The step of shaping or sculpturing before curing is cumbersome, as is grinding after curing. Furthermore, shrinkage of the resin during curing produces strain on the tooth and can result in marginal leakage. Even when shrinkage is minimized by incremental curing and the dentist has sufficient skill to sculpture the uncured resin to duplicate the original tooth contour precisely, the procedure is sufficiently demanding and time consuming that the dentist may prefer the convenience of an amalgam.

It has been suggested that the effect of resin shrinkage can be minimized by using a model or die to form an extra-oral prosthetic dental restoration such as an inlay. Such a model can be formed from dental or gypsum stone (Plaster of Paris), from thermoplastic resin as in U.S. Pat. No. 2,135,404 (Wheeler), or from epoxy resin as illustrated in Jensen et al., "Polymerization Shrinkage and Microleakage," a paper published in *Posterior Composite Resin Dental Restorative Materials* edited by Vanherle et al., pages 243-262 (Peter Szulc Publishing Co., The Netherlands, 1985). The Jensen article in a table at page 258 lists advantages and disadvantages of each of in-the-mouth and out-of-the-mouth "'inlay' posterior composites," the advantages of the latter being:

"Reduced stress on cusps from polymerization shrinkage

Better marginal adaptation at gingivo-proximal (no overhang)

Control of proximal contacts

Better contours and anatomy

Easier to obtain a better surface finish

Possible increased abrasion resistance because resin can be heat cured under vacuum"

Among the listed disadvantages of the out-of-the-mouth or extra-oral "'inlay' posterior composite" are that normally more than one dental appointment is required, thus requiring a temporary restoration, and that there is increased cost due to laboratory procedures.

While the Jensen article refers to the use of an epoxy die for molding dental restorations, and the Wheeler patent refers to the use of dental patterns made from certain thermoplastic resins, such dies or patterns are more commonly made from dental or gypsum stone. Gypsum stone is generally regarded as the state of the art molding material against which other materials are measured. The thermoplastic resins of the Wheeler patent are said to be grindable but must be melted at fairly high temperatures. This can cause unacceptable shrinkage of the model and poor restoration fit. Like epoxy resin, gypsum stone takes a long time to harden, thus requiring two visits to the dentist and a temporary restoration between visits. The need for two visits can be exceedingly inconvenient to patients who live in remote areas, and the need for a dentist to use a dental laboratory can be troublesome when the closest laboratory is at a distant location.

SUMMARY OF THE INVENTION

The present invention permits an extra-oral prosthetic dental restoration to be made in a single visit. It can enable attainment of the advantages quoted above from the Jensen article, while eliminating or minimizing the above-mentioned disadvantages. The invention can also be used for nondental restoration work to provide a durable model that can be used within minutes after it is made. These advantages are achieved by a method comprising the steps of:

(1) forming a rubbery, heat-resistant impression of an object to be duplicated (e.g., a tooth, teeth, gingival or gum tissue, or other animate or inanimate object), (2) partially filling the impression, e.g., coating or dusting all or a part of the working (e.g., tooth) surfaces of the impression, with a liquid or powdered thermosetting resin, (3) further filling said impression with a molten thermoplastic resin and, after the thermoplastic resin solidifies and the thermosetting resin is thermoset, (4) removing the thermoset resin and solidified thermoplastic resin from said impression to provide a model of said object.

The thermoset surfaces of the model can be machined more readily than a model made entirely from thermoplastic resin. This is important when the model is of human teeth, because it often is necessary to grind off material, e.g., at the gingival margins. A surface of cured thermoset resin is also useful when the model is to be used to shape a dental or nondental restoration, because the thermoset resin typically will exhibit good wear resistance. This is important when the restoration is repeatedly installed on and removed from the model and especially important when the restoration comprises a metal such as gold. Because the thermoplastic portion of the model need not be made excessively heat- or abrasion-resistant, thermoplastic resin with optimal melting temperatures and shrinkage can be employed. In addition, the cure rate of the thermosetting resin is greatly enhanced when the impression is filled with molten thermoplastic resin in step (3), thus rapidly polymerizing the thermosetting resin to a tough, abrasion- and heat-resistant state, and enabling the model to be used within minutes after it is molded.

The model produced by the above 4-step model-making method is itself believed to be novel and has a variety of dental and nondental uses. For example, the foregoing steps can be followed by the steps of:

(5) applying restorative resin to a portion of the restoration is required (usually after first applying a release agent to the model), (6) shaping or sculpting the applied restorative model where resin to a desired contour, and (7) curing the restorative resin to provide a restoration.

When the restoration is a dental restoration and is cemented into the patient's mouth, the cement can compensate for polymerization shrinkage of the material used to make the restoration and thus provide good assurance against microleakage. The same 7-step method can be used for nondental restorations, for example, to repair art objects such as marble statues, especially where the restoration should have the same form and contour as the object being restored.

A primary advantage of the novel method and model in dental use is that the model can be made far more quickly than the gypsum or epoxy models that are currently in use. Thus a model of a tooth or teeth can be prepared, used to make a prosthetic dental restoration, and the restoration can be bonded to the tooth or teeth, all in a single visit to the dentist. This eliminates any need for a temporary restoration. While the impression-forming step (1) of the novel model-making method requires the same length of time as do methods used for current extra-oral restorations: steps (2) and (3) of the method provide a substantial time saving in that a combination of thermoset and thermoplastic resins can harden much faster (e.g. within a few minutes) than can gypsum stone or models made entirely of epoxy resin. An additional advantage is that a dental auxiliary (rather than a dentist) can carry out steps (2) through (7). Meanwhile the dentist can work on another patient, returning to the first patient when it is time to install the restoration. This can reduce cost, since the training and skill of a dentist customarily commands a wage far greater than that of a dental auxiliary. While the same cost reduction is available in current extra-oral restorations, that reduction may be more than offset by the cost of transfering impressions or models between the dentist's office and a dental laboratory and scheduling an extra patient visit.

In a preferred embodiment, the novel model-making method can be modified by including between steps, (3) and (4) an additional step of adhering a flexible, dimensionally, stable support to the thermoplastic resin. Models made by this modified method can be flexed by hand (or cut with a knife or other sharp instrument) to form in the solidified thermoplastio resin clean cracks at one or more locations (e.g., in the interproximal spaces flanking a replica tooth). With the flexible support serving as a hinge, the model then can be opened at those cracks to isolate and expose a portion of the model (e.g., the mesial and distal surfaces of a replica tooth). In this fashion the model can be easily manipulated to facilitate access to a portion of the model, e.g., a single replica tooth.

DETAILED DESCRIPTION

Figure 1:
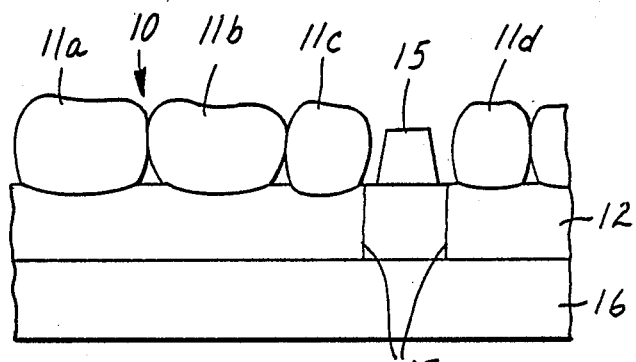
FIG. 1 is a side elevation of a first model made in accordance with the invention.

Referring to FIG. 1, a rubbery poly(vinyl siloxane) dental impression material (not shown) has been used to mold a model 10 having replica teeth 11a, 11b, 11c and 11d, all made from a thermoset resin, and gingival tissue 12, made from a first thermoplastic resin. Bonded to the base of the replica gingival tissue 12 is a flexible support 16, preferably a second thermoplastic resin that is tough and flexible. The replica teeth are tough and have good heat- and abrasion-resistance. Their rate of polymerization (cure) was accelerated by contact with the first thermoplastic resin in its molten state.

Illustrating a preferred embodiment of the invention, two cracks 17 have been initiated in the replica gingival tissue 12 at each side of the replica stump 15. This is readily accomplished by scoring the first thermoplastic resin with a razor blade, and then flexing the model to propagate the cracks.

Figure 2:
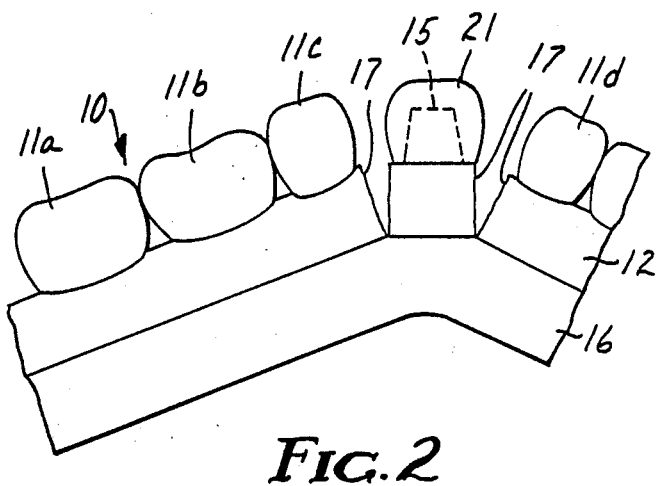
FIG. 2 shows the model of FIG. 1 flexed to expose proximal regions of one of the replica teeth on which a prosthetic dental restoration can be created.

The model is shown in FIG. 2 in its flexed position, providing ready access to replica stump 15 (shown in phantom). Restoration 21 (a full crown) is shown in its installed position on replica stump 15. Interproximal contacts between restoration 21 and adjacent thermoset replica teeth 11c and 11d can be checked by returning the model to the original unflexed position shown in FIG. 1.

The first thermoplastic resin preferably is cleanly breakable to facilitate isolation of replica tooth stump 15. By "cleanly breakable" is meant that when a panel of the thermoplastic resin 1.27 cm (½ inch) in thickness is scored and flexed by hand at room temperature, it will break at the score to form two mating surfaces without visibly apparent elongation.

Figure 3:
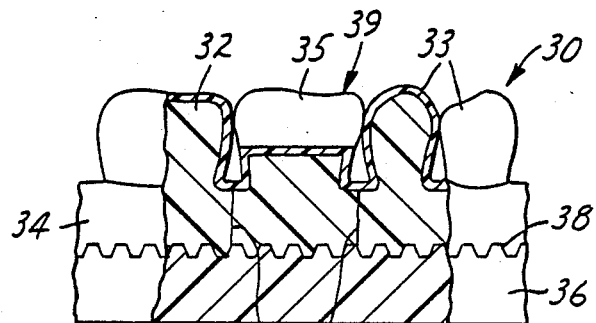
FIG. 3 is a side elevation of a second model of the invention, cut away to a central section.

In FIG. 3, each replica tooth of a model 30 (which was formed from a rubbery dental impression, not shown) has a core 32 of a first thermoplastic resin and a thin shell 33 of a thermoset resin that provides good abrasion- and heat-resistance. The thermoset resin can be formed in place by inverting the impression and coating the replica tooth surfaces and the gingival margin portion of the model with uncured thermoset resin in liquid or powder form. The first thermoplastic resin is then added to the impression in molten form and permitted to harden. Heat from the molten first thermoplastic resin accelerates the cure of the thermoset resin. The first thermoplastic resin provides the bulk of the replica teeth and replica gingival tissue 34, thus providing a cost savings and rapid hardening. However, the thermoset shell 33 provides wear resistance and facilitates removal by grinding of replica gingival tissue, to provide good access for trial installation of a restoration. Bonded across the base of the replica gingival tissue 34 opposite to the replica teeth is a flexible support 36 of tough and flexible second thermoplastic resin that can act as a hinge at cracks 37 through the replica gingival tissue, thus permitting the model 30 to function in the same manner as shown in FIGS. 1 and 2. The flexible support 36 has serrations 38 and is pressed as a preformed solid strip into the molten first thermoplastic resin forming the replica gingival tissue 34. The serrations and relatively weak bond between the first and second thermoplastic resins permit a replica prepared tooth 35 and replica gingival tissue between the cracks 37 to be removed as a unit 39 from the model 30, the unit being repeatedly returnable to its exact original position.

The impression material from which a mold of the object to be duplicated is formed, and in which the model is molded, is a rubbery curable material having sufficient heat resistance to withstand the heat of the molten thermoplastic resin. Suitable impression materials include addition cure or condensation cure silicones, polyethers and polysulfides. The silicones are preferred, since the polyethers and polysulfides generally require the use of a release agent to facilitate removal of the hardened model. Alginates and hydrocolloids are at present unsuitable, since they do not have sufficient heat resistance.

The thermosetting resin should be a one-part or multi-part thermally curable resinous material that is sufficiently tough and sufficient heat-and abrasion-resistant in its cured state to enable the model to be waxed or subjected to repeated trial fits of a restorative. Best results have been achieved when the thermosetting resin has been a two-part epoxy resin, but excellent results have also been achieved when the thermosetting resin has been a two-part urethane resin. Other useful thermoset resins are described in "Powder Coatings", *Kirk-Othmer Encyclopedia of Chemical Technology*, 3d. Ed., Vol. 19, pp. 1–27 (1982), and include polyurethanes and polyacrylics. Phenolic resins also can be used. The thermosetting resin may be applied as a liquid or a powder at elevated or room temperature. Preferably it forms a thin shell on one or more working surfaces of the model, and has a thickness of less than about 2 mm. For dental models, the thermosetting resin can form an outer shell or the whole of the replica teeth, and/or a portion of the replica gingival tissue if desired.

The first thermoplastic resin is, as noted above, preferably cleanly breakable. Useful cleanly breakable thermoplastic resins which have good dimensional stability include aromatic thermoplastic resins such as copolymers of vinyltoluene and alpha-methylstyrene, polyamides, and polyesteramides. The ability of a panel of the resin to break cleanly can be enhanced by adding fillers such as quartz, glass microbubbles, aluminum powder, carbon black, titanium dioxide, or microcrystalline waxes. Clean breakability also can be enhanced by the addition of glassy modifiers such as rosin, rosin esters, aliphatic hydrocarbon resins, aromatic hydrocarbon resins, polyterpenes and combinations thereof.

The first thermoplastic resin preferably hardens as rapidly as possible, coincident with maintenance of adequate dimensional stability and other desired physical properties. Hardening can, if desired, be accelerated by quenching the model in a suitable cooling medium (e.g., water) while the first thermoplastic resin hardens.

The flexible support optionally used between steps (3) and (4) of the method is, as noted above, preferably a second thermoplastic resin that is tough and flexible. The support also may be a fabric (woven or nonwoven) which can be impregnated with a resin, a plastic film such as polypropylene or oriented poly(ethylene terephthalate), an adhesive tape, leather, or rubber. The support can be filled, e.g., with magnetizable particles to secure the model releasably to a metal sheet such as a metal wing of an articulating jig. The preferred tough and flexible second thermoplastic resin can simply be poured to form a layer over the first-mentioned thermoplastic resin, or can, as noted above, be applied as a preformed solid strip while the first-mentioned thermoplastic resin is molten. The preformed strip may, if desired, be formed with serrations or knobs.

Useful second thermoplastic resins are sufficiently tough and flexible to permit repeated (e.g., half a dozen times or more) flexing of the model between the positions shown in FIGS. 1 and 2 without causing apparent distortion of the model. Such resins include ethylene/vinyl acetate copolymers, styrene-butadiene block copolymers, butyl elastomers and polyamides, any of which may be compounded with resins, plasticizers, extenders and fillers to provide desired physical properties such as flexibility, adhesion, and dimensional stability.

Dental models of the invention may be used to make any prosthetic dental restoration including inlays, onlays, veneers, crowns, and bridges. While each of these can be made entirely from dental restorative or composite resin, other useful restorative materials such as metals (e.g., gold), ceramics (e.g., porcelain), and metal-ceramic combinations can be formed on the novel models disclosed above. Pins or other repositionable locating means (optionally coated with a suitable release agent) can be installed in the model if desired, to facilitate removal and replacement of individual model teeth.

In the following examples of thermoplastic and thermosetting resins and models of the invention, all parts are by weight.

Thermosetting Resin A

This two-part epoxy resin is a liquid having a gel time of 4 minutes at 21° C. It contains the following ingredients:

Thermoplastic Resin E

Using the same procedure the following ingredients were mixed with heating and stirring:

| Ingredient | Parts |
| --- | --- |
| "Piccotex" 100 | 240 |
| Ethylene/vinyl acetate copolymer, 18% vinyl acetate ("Elvax" 410, E. I. du Pont de Nemours) | 88 |
| Modified rosin, acid No. 94 ("Regalite" 355, Hercules) | 160 |
| "Imsil" A-25 | 246.4 |
| "Ti-Pure" R-960 | 40 |
| Red iron oxide | 1.6 |
| Hollow glass microbubbles, avg. density 0.23 g/cm³ (3M) | 24 |

Linear shrinkage of a bar of the resulting Thermoplastic Resin E was 0.056 cm (0.022 in.) or 0.44%.

EXAMPLE 1

A dental model was made as illustrated in FIG. 3. The teeth were replicated substantially entirely from thermosetting resin and the gingival tissue was replicated substantially entirely from two thermoplastic resins. The model was formed using a rubbery dental poly(vinyl siloxane) impression material ("Express" Type 1, 3M) molded upon a "Typodont" model ("R862", Columbia Dentoform) of two molar and two bicuspid teeth. One of the molar teeth had been prepared to receive a standard MOD restoration. Using a double-barrelled syringe equipped with a static mixer ("EPX", 3M), Thermosetting Resin A was injected into the impression to approximately the gingival margins. Over this, Thermoplastic Resin E was injected from a hot melt gun ("Polygun" TC, 3M) at a melting chamber temperature of approximately 199° C. (390° F.). While Thermoplastic Resin E about 12 minutes with continued mixing followed by removal of the resin and casting into a slug mold suitable for use in a hot melt gun. The slugs were identified as "Thermoplastic Resin B".

Linear shrinkage of a bar of Thermoplastic Resin B (molded in the mold used for Thermosetting Resin (A) was 0.52%. The bar was cleanly breakable when flexed by hand.

Thermoplastic Resin C

Using the same procedure used for Thermoplastic Resin B, the following ingredients were mixed with heating and stirring:

| Ingredient | Parts |
|---|---|
| "Piccotex" 100 | 150 |
| Microcrystalline wax, m.p. 84–87° C. ("Bowax" 993, Boler Chemical) | 34 |
| "Imsil" A-25 | 200 |
| "Ti-Pure" R-960 | 10 |

Linear shrinkage of a bar of the resulting Thermoplastic Resin C was 0.043 cm (0.017 in.) or 0.34%.

Thermoplastic Resin D

Using the same procedure, the following ingredients were mixed with heating and stirring:

| Ingredient | Parts |
|---|---|
| "Piccotex" 100 | 370 |
| Polyethylene glycol dibenzoate ("Benzoflex" 2-45, Velsicol) | 30 |
| "Imsil" A-25 | 250 |
| "Ti-Pure" R-960 | 200 |
| Carbon Black ("Sterling" R-V7688, Cabot) | 3 |

Linear shrinkage of a bar of the resulting Thermoplastic Resin D was 0.005 cm (0.002 in.) or 0 04%.

| | Parts |
|---|---|
| Part A: | |
| Poly(glycidyl ether) of Bisphenol A having an epoxide equivalent weight of about 200 ("Epon" 828, Shell) | 100 |
| Silicon dioxide, mean particle size 4.3 micrometers ("Imsil" A-25, Illinois Mineral) | 20 |
| Titanium dioxide, Sp. gravity 3.8–4.3 ("Ti-Pure" R-960, E. I. duPont de Nemours) | 5 |
| Fluorocarbon surfactant ("Fluorad" FC-430, 3M) | 0.5 |
| Part B: | |
| Polymercaptan ("Capcure" 3-800, Diamond Shamrock) | 90 |
| Dimethylaminomethyl phenol ("DMP-30"., Rohm & Haas) | 10 |
| "Imsil" A-25 | 20 |
| "Ti-Pure" R-960 | 5 |
| "Fluorad" FC-430 | 0.5 |

A slug of Thermosetting Resin A was cast into a bar 12.73×1.31×1.27 cm (5.012×0.516×0.500 inches). Linear shrinkage of the bar in the long dimension was 0.13%.

Thermoplastic Resin B

Using a hot plate (Corning PC-35) and a band heater (Tempco Electric Heater Corp.), 50 parts of modified hydrocarbon-based resin, acid No. 90–100 ("Pexalyn" A500, Hercules) were melted at a temperature of about 171° C. (340° F.). While stirring with an air mixer, 150 parts of a copolymer of vinyltoluene and alpha-methylstyrene ("Piccotex" 100, Hercules) were added to the melt. When a homogeneous mixture had been obtained, 225 parts of "Imsil" A-25 were added incrementally using high-shear mixing, followed by incremental additions of 30 parts "Ti-Pure" R-960. The temperature was raised to 232° C. (450° F.) for was still molten, a serrated strip of tough and flexible thermoplastic resin was pressed into the molten resin. The strip was about 100 mm in width, 5 mm in average thickness, and 40 mm in length and was made by molding a hot melt adhesive having a Brookfield viscosity of 5,000 cps at 191° C. (375° F.), a tensile strength of 2.76 MPa (400 psi) and an elongation of 750% ("Jet-Melt" 3792 hot melt adhesive, 3M) in a mold with a serrated face. After 10 minutes, Thermoplastic Resin E had hardened, Thermosetting Resin A had been cured by heat from the thermoplastic resin, and the resulting model could be removed from the dental impression. An excellent replica was obtained. Its replica tooth areas were readily cut away with a bur. When a heated waxing spatula at a temperature of about 260° C. (500° F.)-was laid upon the replica teeth for several seconds, no damage to the teeth was noticed.

The model could be used to create dental restorations such as inlays by injecting dental restorative or composite resin into the cavity of the replica prepared molar. To facilitate doing so, the replica gingival tissue formed by Thermoplastic Resin E was scored at the mesial and distal sides of the replica prepared molar. Then upon flexing the model by hand, the replica gingival tissue broke cleanly at each score, permitting the model to be hingedly opened in the manner shown in FIG. 2 of the drawing. By grasping the replica prepared molar between the fingers, it and the replica gingival tissue between the cracks were separated from the serrated surface and lifted out to form a unit similar to unit 39 in FIG. 3, but having a replica molar formed entirely of thermosetting resin.

EXAMPLE 2

A dental model was made as described in Example 1 except that instead of injecting a liquid thermosetting resin, a thermosetting epoxy resin powder ("Scotchkote" 203, 3M) was sprinkled into the inverted dental impression from a plastic squeeze bottle. To facilitate application of the powder, the impression had been preheated in an oven at 65° C. The dental impression was turned over, allowing excess powder to fall out, and leaving a uniform layer of powder covering the tooth surfaces and adjacent portions of the gingival surfaces.

The impression was once again inverted. Onto the layer of powder, Thermoplastic Resin E was injected from a hot melt gun as in Example 1 to fill both the tooth and gingival portions of the impression. A serrated strip of tough and flexible thermoplastic resin as used in Example 1 was pressed into the molten Thermoplastic Resin E. The model was allowed to cool, hardening within 10 minutes, at which time the model could be removed from the dental impression and put to immediate use to create a dental restoration. The thermosetting epoxy resinpowder had been fused and cured by the heat of the molten Thermoplastic Resin E to provide a thermoset shell having a uniform thickness of approximately 1 mm. Surfaces of the model that had been covered by the thermoset shell were readily cut away with a bur. When a heated waxing spatula touched the shell for several seconds, no damage to the teeth was noticed.

EXAMPLE 3

A dental model was made using a rubbery dental impression as in Example 1. Then using a double-barrelled syringe as in Example 1, a two-part thermosetting urethane resin composition (-"Dyna-Cast", Kindt-Collins) was injected into the impression to approximately the gingival margins. Immediately thereafter, a tough and flexible thermoplastic resin having a Brookfield viscosity of 14,500 cps at 191° C. (375° F.), a tensile strength of 3.3 MPa (475 psi), and an elongation of 600% ("Jet-Melt" 3758 adhesive, 3M) was injected from a hot melt gun into the impression to fill the gingival portion of the impression. After cooling for about 10 minutes, the resulting model was removed from the impression and was ready for immediate use in making dental restorations. The model was an excellent replica, its thermosetting resin having been cured by heat from the thermoplastic resin. The replica teeth of thermoset urethane resin could be readily cut away with a bur. When a heated waxing spatula touched the replica teeth for several seconds, no damage to the teeth was noticed.

The replica gingival tissue of the model was cut on either side of the replica prepared molar to about half of the gingival tissue thickness of 12 mm. The uncut replica gingival tissue then served as a hinge to provide good access to the proximal surfaces of the replica tooth and to return the row of replica teeth approximately to the original configuration. Even though the opposing surfaces at the cuts did not precisely mate with one other, the resulting inaccuracy was deemed to be of only minor significance in the formation of typical restorations.

Various modifications and alterations of this invention will be apparent to those skilled in the art without departing from the scope and spirit of this invention and the latter should not be restricted to that set forth herein for illustrative purposes.

I claim:

1. A hardenable model of an object useful for making a restoration for the object, said model having at least one surface portion of thermosetting resin which is not substantially thermoset, said model further comprising molten thermoplastic resin in contact with said thermosetting resin, said thermoplastic resin being cleanly breakable at room temperature upon hardening.

2. A model as defined in claim 1, which replicates gingival tissue and a row of teeth.

* * * * *